United States Patent [19]
Tzou et al.

[11] Patent Number: 5,980,867
[45] Date of Patent: Nov. 9, 1999

[54] FLUNISOLIDE AEROSOL FORMULATIONS

[75] Inventors: Tsi-Zong Tzou, Lake Elmo; Robert K. Schultz, Edina; Danna L. Ross, Pine Springs, all of Minn.

[73] Assignee: 3M Innovative Prperties Company, St. Paul, Minn.

[21] Appl. No.: 09/110,796

[22] Filed: Jul. 6, 1998

Related U.S. Application Data

[63] Continuation of application No. 08/456,029, May 31, 1995, Pat. No. 5,776,433, which is a continuation of application No. 08/170,509, Dec. 20, 1993, abandoned.

[51] Int. Cl.$^6$ ............................................. A61K 9/12
[52] U.S. Cl. ...................................... 424/45; 424/46
[58] Field of Search ..................... 424/45, 46; 514/958, 514/959

[56] References Cited

U.S. PATENT DOCUMENTS

| | | | |
|---|---|---|---|
| 2,868,691 | 1/1959 | Porush et al. | 167/54 |
| 2,885,427 | 5/1959 | Ruh et al. | 260/653.7 |
| 4,083,954 | 4/1978 | Tsuchiya et al. | 424/47 |
| 4,174,295 | 11/1979 | Bargigia et al. | 252/305 |
| 4,243,548 | 1/1981 | Heeb et al. | 252/305 |
| 4,273,710 | 6/1981 | Jones et al. | 260/239.55 |
| 4,814,161 | 3/1989 | Jinks et al. | 424/45 |
| 4,851,211 | 7/1989 | Adjei et al. | 424/40 |
| 4,933,168 | 6/1990 | Jones et al. | 424/45 |
| 4,983,312 | 1/1991 | Tamura et al. | 252/67 |
| 4,983,595 | 1/1991 | Benjamin et al. | 514/174 |
| 5,118,494 | 6/1992 | Schultz et al. | 424/45 |
| 5,182,097 | 1/1993 | Byron et al. | 424/45 |
| 5,190,029 | 3/1993 | Byron et al. | 128/200.14 |
| 5,202,110 | 4/1993 | Dalby et al. | 424/45 |
| 5,225,183 | 7/1993 | Purewal et al. | 424/45 |
| 5,674,471 | 10/1997 | Akehurst et al. | . |
| 5,695,743 | 12/1997 | Purewal et al. | . |
| 5,776,433 | 7/1998 | Tzou et al. | . |

FOREIGN PATENT DOCUMENTS

| | | |
|---|---|---|
| 0384371 A1 | 8/1990 | European Pat. Off. . |
| 0504112 A2 | 9/1992 | European Pat. Off. . |
| 4123663 A1 | 1/1993 | Germany . |
| 91/11495 | 8/1991 | WIPO . |
| 91/11496 | 8/1991 | WIPO . |
| 91/14422 | 10/1991 | WIPO . |
| 92/06675 | 4/1992 | WIPO . |
| 92/22287 | 12/1992 | WIPO . |
| 92/22288 | 12/1992 | WIPO . |
| 93/11747 | 6/1993 | WIPO . |

OTHER PUBLICATIONS

"Comparison of Output Particle Size Distributions from Pressurised Aerosols Formulated as Solutions or Suspensions" (R.N. Dalby and P.R. Byron, *Pharmaceutical Res.*, vol. 5, No. 1 (1988) p. 36).

*The Theory and Practice of Industrial Pharmacy*, Leon Lachman et al., 3rd Ed., Lea & Febiger 1986, Chapter 20, p. 597, 599 and 603.

*The Theory and Practice of Industrial Pharmacy*, 2nd Edition, 1976, Lea & Febiger, Philadelphia, pp. 270 and 276–280.

Gennaro, A.R. (1985), Remington's Pharmaceutical Sciences, Mack Publishing Co., pp. 1670–1677.

Marin, F. et al. (1993), Aerosols in Medicine: Principles, Diagnosis and Therapy, Elsevier, pp. 303–319.

*Primary Examiner*—Raj Bawa
*Attorney, Agent, or Firm*—Ted K. Ringsred; MarySusan Howard; Robert W. Sprague

[57] ABSTRACT

Pharmaceutical aerosol formulations comprising flunisolide, ethanol, and a propellant selected from the group consisting of 1,1,1,2-tetrafluoroethane, 1,1,1,2,3,3,3-heptafluoropropane, and a mixture thereof.

19 Claims, No Drawings

FLUNISOLIDE AEROSOL FORMULATIONS

This is a continuation of application Ser. No. 08/456,029 filed May 31, 1995, now U.S. Pat. No. 5,776,433, which is a continuation of 08/170,509, filed Dec. 20, 1993, now abandoned.

BACKGROUND OF THE INVENTION

1. Field of the Invention

This invention relates to pharmaceutical aerosol formulations. In another aspect this invention relates to pharmaceutical solution aerosol formulations wherein the propellant comprises 1,1,1,2-tetrafluoroethane or 1,1,1,2,3,3,3-heptafluoropropane. In another aspect this invention relates to pharmaceutical aerosol formulations containing flunisolide.

2. Description of the Related Art

Flunisolide (6α-fluoro-11β,16α,17,21-tetrahydroxypregna-1,4-diene-3,20-dione cyclic 16,17-acetal with acetone) is an antiinflammatory steroid. NASALIDE™ Nasal Solution (Syntex Laboratories, Inc.) is a flunisolide formulation for administration as a spray to the nasal mucosa (e.g., for topical rhinitis treatment). It contains flunisolide in a solution of propylene glycol, polyethylene glycol 3350, citric acid, sodium citrate, butylated hydroxyanisole, edetate disodium, benzalkonium chloride, and purified water, with sodium hydroxide and/or hydrochloric acid added to adjust the pH to approximately 5.3. AEROBID™/AEROBID-M Inhaler (Forest Pharmaceuticals, Inc.) is a metered dose aerosol system containing a microcrystalline suspension of flunisolide as the hemihydrate in CFC propellants (trichloromonofluoromethane, dichlorodifluoromethane and dichlorotetrafluoroethane) with sorbitan trioleate as a dispersing agent. AEROBID-M also contains menthol as a flavoring agent.

Current propellant-based pharmaceutical aerosol formulations, such as the above-described AEROBID™ Inhalers, use a mixture of liquid chlorofluorocarbons as the propellant. Fluorotrichloromethane, dichlorodifluoromethane and dichlorotetrafluoroethane are the most commonly used propellants in aerosol formulations for administration by inhalation. Such chlorofluorocarbons (CFCs), however, have been implicated in the destruction of the ozone layer and their production is being phased out. Hydrofluorocarbon 134a (HFC 134a, 1,1,1,2-tetrafluoroethane) and hydrofluorocarbon 227 (HFC 227, 1,1,1,2,3,3,3-heptafluoropropane) are viewed as being more ozone friendly than many chlorofluorocarbon propellants.

SUMMARY OF THE INVENTION

Flunisolide hemihydrate has been found to have appreciable solubility in HFA 134a, HFA 227 or mixtures thereof (HFA 134a dissolves about 0.006% by weight of flunisolide hemihydrate; HFA 227 dissolves about 0.004% by weight of flunisolide hemihydrate; and a 1:1 volume to volume blend of HFA 134a and HFA 227 dissolves about 0.007% by weight flunisolide hemihydrate). This intermediate level of solubility can lead to particle size increase of the drug in a suspension formulation. It is well known that particles having a diameter of greater than about 10 μm are not suitable for inhalation to the lung. Therefore particle size increase can threaten the utility of a pharmaceutical aerosol formulation.

The present invention provides a solution aerosol formulation comprising a therapeutically effective amount of flunisolide, a propellant comprising a hydrofluorocarbon selected from the group consisting of 1,1,1,2-tetrafluoroethane, 1,1,1,2,3,3,3-heptafluoropropane, and a mixture thereof, and ethanol in an amount effective to solubilize the flunisolide in the formulation.

The present invention also provides a method of treating bronchial asthma, comprising administering via inhalation an amount of the formulation as described above effective to treat bronchial asthma.

The use of a solution formulation of the invention eliminates the problems associated with an increase of particle size. This invention also eliminates other problems encountered with suspension aerosols such as rapid flocculation, irreversible particle aggregation and bulk separation (creaming or settling); all of which affect dose uniformity. Moreover a formulation of the invention provides a higher respirable fraction of drug than does the currently available suspension aerosol formulation of flunisolide based on CFC propellants.

DETAILED DESCRIPTION OF THE INVENTION

All weight percentages recited herein are based on the total weight of the formulation unless otherwise indicated.

The medicament flunisolide is known and disclosed, e.g., in U.S. Pat. No. 4,933,168 (Jones et al.). Flunisolide is generally present in a formulation of the invention in a therapeutically effective amount, i.e., an amount such that one or more metered volumes of the formulation when delivered to the lung by oral or nasal inhalation contains an amount of medicament effective to exert the intended therapeutic action. Preferably the medicament constitutes about 0.1 to about 0.9 percent by weight, more preferably about 0.2 to about 0.6 percent by weight of the total weight of the formulation.

The formulation of the invention is a solution formulation, i.e., the flunisolide is substantially fully dissolved in the formulation and the formulation is substantially free of undissolved flunisolide. Flunisolide has been known to exist in several polymorphic forms. A formulation of the invention, however, contains flunisolide but not a particular polymorphic form thereof, as such polymorphic forms lose their crystalline identity when in solution. Therefore this invention avoids complications that can occur in certain suspension steroid formulations due to in situ changes in crystal form (e.g., crystal polymorphism). Also any appropriately soluble polymorphic form of flunisolide (e.g., flunisolide hemihydrate) can be used in preparing a formulation of the invention.

A formulation of the invention contains ethanol in an amount effective to solubilize the flunisolide in the formulation. Preferably the ethanol constitutes about 3 to about 30 percent by weight of the total weight of the formulation. More preferably, ethanol constitutes about 10 to about 20 percent by weight of the aerosol formulation.

The hydrofluorocarbon propellant can be 1,1,1,2-tetrafluoroethane, 1,1,1,2,3,3,3-heptafluoropropane, or a mixture thereof in any proportion. The propellant is present in an amount sufficient to propel a plurality of doses from an aerosol canister such as a metered dose inhaler. The propellant preferably constitutes from about 68 to about 97 percent by weight, and more preferably from about 75 to about 87 percent by weight of the total weight of the aerosol formulation. The formulations of the invention are preferably free of chlorofluorocarbon propellants such as fluorotrichloromethane, dichlorodifluoromethane, and dichlorotetrafluoroethane. Most preferably, the hydrofluorocarbon propellant is the only propellant present in the formulations of the invention.

A formulation of the invention can contain suitable excipients (e.g., those disclosed in U.S. Pat. No. 5,225,183, Purewal, et al.) in amounts readily determined by those skilled in the art. Certain excipients, e.g., certain surfactants, flavoring agents, and/or water, are beneficial to some embodiments of the invention. For example, it has been found that the chemical stability of certain formulations of the invention (that is, stability of the formulation to degradation of flunisolide) is enhanced by the presence of water. When water is included in a formulation of the invention it will generally be present in an amount of about 0.005 percent to about 1 percent by weight of the total weight of the formulation.

It has also been found that the chemical stability of certain formulations of the invention is enhanced by the presence of sorbitan trioleate. When sorbitan trioleate is included in a formulation of the invention it will generally be present in an amount of about 0.001 percent to about 0.1 percent by weight of the total weight of the formulation.

It has also been found that the chemical stability of certain formulations of the invention is enhanced by the presence of cetylpyridinium chloride. When cetylpyridinium chloride is included in a formulation of the invention it will generally be present in an amount of about 0.001 percent to about 0.2 percent by weight of the total weight of the formulation.

Formulations of the invention optionally further comprise a flavoring agent. A preferred flavoring agent is menthol. In an embodiment of the invention comprising menthol, menthol is preferably present in an amount effective to mask the taste of flunisolide when an aerosolized dose of the formulation is inhaled orally, e.g., about 0.3 percent by weight of the total weight of the formulation.

Formulations of the invention can be prepared by either pressure filling or cold filling techniques, both of which are well known to those skilled in the art. Ethanol and the excipient or excipients, if any, are combined with the propellant and then this solution is pressure filled or cold filled into aerosol vials containing the flunisolide. Alternatively, the flunisolide and any non-volatile excipients are dissolved in ethanol in an aerosol vial. The aerosol vial is then fitted with a valve and pressure filled with the propellant.

Aerosol canisters equipped with conventional valves, preferably metered dose valves, can be used to deliver formulations of the invention. It has been found, however, that selection of appropriate valve assemblies for use with aerosol formulations is dependent upon the particular excipients used (if any), on the propellant, and on the medicament being used. Conventional neoprene and buna valve rubbers used in metered dose valves for delivering conventional chlorofluorocarbon (CFC) formulations often have less than optimal valve delivery characteristics and ease of operation when used with formulations containing 1,1,1,2-tetrafluoroethane or 1,1,1,2,3,3,3-heptafluoropropane. Moreover, conventional CFC formulations generally contain a surfactant or lubricant. Some formulations of the invention, however, do not contain a surfactant or a lubricant. Therefore certain formulations of the invention are preferably dispensed via a valve assembly wherein the diaphragm is fashioned by extrusion, injection molding or compression molding from a thermoplastic material such as FLEXOMER™ GERS 1085 NT polyolefin (Union Carbide). Another suitable valve rubber is a nitrile rubber ("DB-218") available from American Gasket and Rubber, Schiller Park, Ill.

Conventional aerosol canisters can be used to contain a formulation of the invention. It has been found, however, that certain containers enhance the chemical stability of certain formulations of the invention and/or minimize the absorption of flunisolide onto the container walls; therefore, it is preferred to contain a formulation of the invention within a glass aerosol vial or an aluminum aerosol vial having an interior formulation chamber coated with a resin that is inert to flunisolide and preferably does not absorb flunisolide from the formulation. Suitable resins for coating the formulation chamber include materials commonly employed as interior can coatings, such as epoxy resins (e.g., epoxy-phenolic resins and epoxy-urea-formaldehyde resins).

A formulation of the invention can be administered to the lung by oral or nasal inhalation. Oral inhalation is preferred, and conventional actuators for oral inhalation can be used in connection with a formulation of the invention. Particle size or droplet size of the inhaled dose is important to an inhalable dose form intended to be administered to the lung. Particle size or droplet size and respirable fraction of a propellant based solution aerosol formulation can be affected by the size of the orifice through which the formulation passes. It is preferred to administer a formulation of the invention through an actuator having an orifice diameter of about 0.25 mm (0.010 inch). An example of such an actuator is actuator model M3756, 3M Company.

The examples set forth below are intended to illustrate the invention.

RESPIRABLE FRACTION

In this assay the respirable fraction (the percent by weight of particles having an aerodynamic particle size of less than 4.7 $\mu$m) of the aerosol formulation is determined using an Anderson Cascade Impactor (available from Anderson Sampler Inc,; Atlanta, Ga.).

The aerosol vial containing the formulation to be tested is primed 5 times. The valve and valve stem are then cleaned with ethanol and dried with compressed air or nitrogen. The aerosol vial and a clean, dry actuator (Model M3756, 3M) are coupled to the glass throat attached to the top of the impactor using an appropriate firing adaptor. The calibrated vacuum pump (28.3 L/min) attached to the impactor is turned on. The vial is actuated. After the aerosol cloud has disappeared (about 4 seconds), the vial and actuator are disconnected, shaken for about 10 seconds, then reconnected to the throat and actuated again. This procedure is repeated until the vial has been actuated a total of 10 times. The cascade impactor is disassembled and each component is rinsed with diluent. Each solution is analyzed for flunisolide content using high performance liquid chromatography or ultraviolet spectroscopy (241 nm). The respirable fraction is calculated as follows:

$$\% \text{ Respirable} = \frac{\text{Flunisolide recovered from plates 3–7}}{\text{Flunisolide recovered from the throat, 0 jet stage and plates 0–7}} \times 100$$

PERCENT DEGRADATION IMPURITIES AND PERCENT DRUG RECOVERY

In this assay the percent of degradation impurities and the percent of drug recovered is determined using high performance liquid chromatography.

SAMPLE SOLUTION PREPARATION

The aerosol vial containing the formulation to be assayed is weighed then chilled in dry ice for 20 minutes. The cap is removed and the contents of the vial are poured into a pre-chilled volumetric flask (100 mL). The propellant is allowed to evaporate. The cap and vial are rinsed with acetonitrile into the volumetric flask. The flask is brought to volume with ethanol or preferably acetonitrile. A portion (2 mL) of this solution is pipetted into a volumetric flask (100 mL) and the flask is brought to volume with mobile phase (The mobile phase is prepared by combining glacial acetic acid (10 mL) with distilled water (990 mL) and combining a portion (650 mL) of the resulting solution with acetonitrile (350 mL)).

STANDARD SOLUTION PREPARATION

Flunisolide hemihydrate (about 32 mg) is placed into a volumetric flask (50 mL) then dissolved in ethanol or preferably acetonitrile. The flask is brought to volume with ethanol or preferably acetonitrile. A portion (2 mL) of this solution is pipetted into a volumetric flask (100 mL) and the flask is brought to volume with mobile phase.

PROCEDURE

A portion (25 μL) of the standard solution is injected into the HPLC (flow rate: 2.0 L/min; column μ-Bondpak C18 (Waters) 30 cm by 3.9 mm; mobile phase as described above; UV detector set at 254 nm) and the recorder sensitivity is adjusted to produce peaks at 70–90% of full scale. The chromatogram is obtained and the peak areas are measured. This chromatogram provides a correlation between the weight of flunisolide and the area of the flunisolide peak. It also provides the peak areas of any impurities which may be present in the raw drug (flunisolide hemihydrate) prior to formulation.

A portion (25 μL) of the sample solution is injected into the HPLC under the same conditions as the standard. The chromatogram is obtained and the peak areas are measured.

CALCULATION OF PERCENT DEGRADATION IMPURITIES

The percent impurities in the raw drug is determined using the peak areas from the chromatogram of the standard solution and the equation below.

$$\frac{\% \text{ impurities}}{\text{in raw drug}} = \frac{\text{Sum of the areas of the impurity peaks}}{\text{Sum of the areas of the impurity peaks and the flunisolide peak}} \times 100$$

The percent impurities in the sample is obtained by performing the same calculation on the peak areas from the sample chromatogram.

The percent degradation impurities is then determined using the equation below.

$$\begin{array}{c} \% \text{ degradation} = \% \text{ impurities in} - \% \text{ impurities in} \\ \text{impurities} \quad \text{the samples} \quad \text{raw drug} \end{array}$$

PERCENT DRUG RECOVERY

This calculation is based on the amount of flunisolide in the sample vial before and after storage.

The amount of flunisolide that was in the aerosol vial after storage is determined using the area of the flunisolide peak from the sample chromatogram and the correlation between weight of flunisolide and the area of the flunisolide peak that is obtained from the standard chromatogram.

The amount of flunisolide that was in the aerosol vial when it was first prepared is known.

The percent drug recovery is then determined using the equation given below.

$$\% \text{ drug recovery} = \frac{\text{amount of flunisolide after storage}}{\text{initial amount of flunisolide}} \times 100$$

EXAMPLE 1

Flunisolide hemihydrate (60 mg) and ethanol (2.25 g) were placed in a 10 mL aluminum aerosol vial. The vial was cooled to about −78° C. in a dry ice/trichloromethane bath then filled with cold P134a (1,1,1,2-tetrafluoroethane, 12.75 g). The vial was sealed with a 50 μL metered dose valve having a diaphragm of DB-218 nitrile rubber (American Gasket and Rubber, Schiller Park, Ill.). The respirable fraction was determined using the test method described above and found to be 55%.

EXAMPLE 2

Flunisolide hemihydrate (61.2 mg) and ethanol (2.25 g) were place in a 10 mL aluminum aerosol vial. The vial was sealed with a continuous valve then pressure filled with P227 (1,1,1,2,3,3,3-heptafluoropropane, 14.55 g). The vial was chilled then the continuous valve was replaced with a 50 μL metered dose valve having a diaphragm of DB-218 nitrile rubber (American Gasket and Rubber, Schiller Park, Ill.). The respirable fraction was determined using the method described above and found to be 43%.

EXAMPLE 3

A bulk propellant solution was prepared by dissolving oleic acid (0.0394 g) and menthol (0.38423 g) in ethanol (19.427) in a 4 ounce (120 mL) glass aerosol vial, crimping a continuous valve onto the vial and then pressure filling with 1,1,1,2-tetrafluoroethane (109.6 g). Flunisolide hemihydrate (about 62 mg each) was placed into 10 mL aluminum aerosol vials which were then sealed with continuous valves that were fitted with gaskets and diaphragms made from FLEXOMER™ GERS 1085 NT polyolefin (Union Carbide). The vials were pressure filled with the bulk propellant solution via a valve to valve transfer button to provide a formulation containing 0.4 percent by weight of flunisolide, 0.03 percent by weight of oleic acid, 0.3 percent by weight of menthol and 15 percent by weight of ethanol. The vials were stored at 40° C. and 85% relative for humidity for 3 weeks then assayed according to the test method described above for percent degradation impurities and percent drug recovery. The results are shown in Table 2 below where each value is the average of 2 separate vials.

EXAMPLES 4–14

Using the general method of Example 3, the aerosol formulations shown in Table 1 below were prepared. Each formulation contained 0.4 percent by weight of flunisolide and 15 percent by weight of ethanol. The percentages in Table 1 are by weight based on the total weight of the formulation. The vials were stored at 40° C. and 85% relative humidity for the time indicated in Table 2 then assayed for percent degradation impurities and percent drug recovery. The results are shown in Table 2 below where, unless otherwise indicated, each value is the average of 2 separate vials.

TABLE 1

| Example Number | Propellant | Excipient(s) |
|---|---|---|
| 4 | 134a | None |
| 5 | 227 | None |
| 6 | 134a | 0.03% oleic acid |
| 7 | 227 | 0.03% oleic acid |
| 8 | 134a | 0.3% menthol |
| 9 | 227 | 0.3% menthol |
| 10 | 227 | 0.3% menthol/0.03% oleic acid |
| 11 | 134a | 0.002% Span ® 85[1] |
| 12 | 227 | 0.002% Span 85 |
| 13 | 134a | 0.3% menthol/0.002% Span 85 |
| 14 | 227 | 0.3% menthol/9.002% Span 85 |

[1]Sorbitan trioleate; Atlas Chemical Inc

TABLE 2

| Example Number | Weeks Stored | % Degradation Impurities | % Drug Recovery |
|---|---|---|---|
| 3 | 3 | 2.58 | 95.4 |
| 4 | 3 | 5.97 | 93.1 |
| 5 | 3 | 1.20 | 98.7 |
| 6 | 3 | 3.89 | 94.5 |
| 7 | 3 | 2.38 | 96.4 |
| 8 | 3 | 1.18 | 97.3 |
| 9 | 3 | 0.88 | 97.9 |
| 10 | 3 | 1.54 | 97.5 |
| 11 | 5 | 1.77[1] | 99.7[1] |
| 12 | 5 | 1.52[1] | 98.1[1] |
| 13 | 5 | 2.63[1] | 98.4[1] |
| 14 | 5 | 2.09[1] | 98.6[1] |

[1]Value obtained from a single vial

EXAMPLES 15–18

Using the general method of Example 3, the aerosol formulations shown in Table 3 below were prepared. Each formulation contained 0.4 percent by weight of flunisolide. The percentages in Table 3 are by weight based on the total weight of the formulation. The vials were stored at 40° C. and 85% relative humidity for 3 weeks then assayed for percent degradation impurities and percent drug recovery. The results are shown in Table 4 below where each value is the average of 2 separate vials.

TABLE 3

| Example Number | Propellant | Excipients |
|---|---|---|
| 15 | 134a | 0.75% water/14.25% ethanol |
| 16 | 227 | 0.75% water/14.25% ethanol |
| 17 | 134a | 0.3% menthol/0.75% water/14.25% ethanol |
| 18 | 227 | 0.3% menthol/0.75% water/14.25% ethanol |

TABLE 4

| Example Number | % Degradation Impurities | % Drug Recovery |
|---|---|---|
| 15 | 0.63 | 97.5 |
| 16 | 0.65 | 96.9 |
| 17 | 0.69 | 95.4 |
| 18 | 0.53 | 95.6 |

EXAMPLE 19

Using the general method of Example 3 except that both glass and aluminum aerosol vials were used, a formulation containing 0.4 percent by weight flunisolide, 15 percent by weight ethanol and P227 was prepared. The vials were stored at 40° C. and 85% relative humidity for the number of weeks indicated in Table 5 then assayed for percent degradation impurities and percent drug recovery. The results are shown in Table 5 below where each value is the average of 2 separate vials.

TABLE 5

| Vial Type | Weeks | % Degradation Impurities | % Drug Recovery |
|---|---|---|---|
| aluminum | 3 | 1.91 | 96.6 |
| aluminum | 8 | 4.63 | 94.0 |
| glass | 3 | 0.84 | 98.8 |
| glass | 8 | 1.73 | 99.7 |

EXAMPLE 20

Using the general method of Example 3 except that both glass and aluminum aerosol vials were used, a formulation containing 0.4 percent by weight flunisolide, 0.3 percent by weight menthol, 15 percent by weight ethanol and P227 was prepared. The vials were stored at 40° C. and 85% relative humidity for the number of weeks indicated in Table 6 then assayed for percent degradation impurities and percent drug recovery. The results are shown in Table 6 below where each value is the average of 2 separate vials.

TABLE 6

| Vial Type | Weeks | % Degradation Impurities | % Drug Recovery |
|---|---|---|---|
| aluminum | 3 | 2.04 | 96.1 |
| aluminum | 8 | 4.49 | 94.7 |
| glass | 3 | 0.81 | 98.4 |
| glass | 8 | 1.52 | 97.1 |

EXAMPLES 21–28

A set of aerosol formulations containing 0.43 percent by weight of flunisolide, 15 percent by weight of ethanol, P227 and various excipients was prepared using the following method. A bulk propellant solution was prepared by placing the excipient and ethanol in a 4 ounce (120 mL) glass bottle, sealing the bottle with a continuous valve and then pressure-filling with P227. The bottle was cooled to −60° C., the continuous valve was removed and the bulk propellant solution was poured into chilled aluminum aerosol vials containing a preweighed amount of flunisolide hemihydrate. The vials were sealed with blind ferrules that were equipped with gaskets made from FLEXOMER™ GERS 1085 NT polyolefin. The identity and amount of excipient present in each formulation is shown in Table 7 below where the percentages are by weight based on the total weight of the formulation. The vials were stored for four weeks at either 40° C. and ambient humidity or at 40° C. and 85% relative humidity then assayed for percent-degradation impurities and percent drug recovery. The results are shown in Table 7 where each value is the average of eight separate vials, four under each storage condition.

TABLE 7

| Example Number | Excipient (s) | % Degradation Impurities | % Drug Recovery |
|---|---|---|---|
| 21 | None | 2.18 | 97.2 |
| 22 | 0.2% CPC[1] | 1.41 | 98.2 |
| 23 | 0.048% Span ® 85[2] | 1.78 | 98.1 |
| 24 | 0.048% Span 85/0.2% CPC | 1.39 | 99.1 |
| 25 | 0.1% oleic acid | 7.41 | 89.9 |
| 26 | 0.1% oleic acid/0.2% CPC | 4.54 | 93.0 |
| 27 | 0.1% oleic acid/0.048% Span 85 | 5.97 | 92.3 |
| 28 | 0.1% oleic acid/0.2% CPC/0.048% Span 85 | 3.89 | 93.4 |

[1]CPC is cetylpyridium chloride
[2]Sorbitan trioleate; Atlas Chemical Inc.

EXAMPLE 29

A bulk propellant solution containing 15 percent by weight of ethanol in P227 was prepared according to the method of Example 21. This solution was cold filled under nitrogen into four different types of aerosol vials which were chilled and contained a preweighed amount of flunisolide hemihydrate. The final formulation contained 0.43 percent by weight of flunisolide. The vials were sealed with blind ferrules equipped with gaskets prepared from FLEX-OMER™ GERS 1085 NT polyolefin. The vials were stored at 40° C. and 85% relative humidity for 5 weeks then assayed for percent degradation impurities and percent drug recovery. The results are shown in Table 8 below where each value is the average of 2 separate vials.

TABLE 8

| Vial Type | % Degradation Impurities | % Drug Recovery |
|---|---|---|
| aluminum[1] | 2.07 | 99.8 |
| plastic[2] | 0.27 | 23 |
| epoxy coated aluminum[3] | 0.14 | 100.6 |
| glass[4] | 1.07 | 100.1 |

[1]Available from 3M Company
[2]Made from polyethylene terephthalate and are available from Precise Plastic Ltd., United Kingdom
[3]Epoxy/phenol-formaldehyde resin coated aluminum vials, coated by Cebal
[4]Made from Type-III (soda-lime) glass and are available from Wheaton Coated Products

What is claimed is:

1. An aerosol formulation comprising: about 0.1 percent to about 0.9 percent by weight of flunisolide in solution; a propellant comprising a hydrofluorocarbon selected from the group consisting of 1,1,1,2-tetrafluoroethane, 1,1,1,2,3,3,3,-heptafluoropropane, and a mixture thereof, and about 3 percent to about 30 percent by weight ethanol in an amount effective to solubilize the flunisolide in the formulation.

2. An aerosol formulation according to claim 1, wherein the propellant comprises 1,1,1,2-tetrafluoroethane.

3. An aerosol formulation according to claim 1, wherein the propellant comprises 1,1,1,2,3,3,3-heptafluoropropane.

4. An aerosol formulation according to claim 1, wherein the propellant comprises a mixture of 1,1,1,2-tetrafluoroethane and 1,1,1,2,3,3,3-heptafluoropropane.

5. An aerosol formulation according to claim 1, characterized in that it is substantially free of chlorofluorocarbon propellants.

6. An aerosol formulation according to claim 1 further comprising about 0.005 percent to about 1 percent by weight water.

7. An aerosol formulation according to claim 1 further comprising about 0.001 percent to about 0.1 percent by weight sorbitan trioleate.

8. An aerosol formulation according to claim 1 further comprising about 0.001 percent to about 0.2 percent by weight cetylpyridinium chloride.

9. An aerosol formulation according to claim 1 further comprising a flavoring agent.

10. An aerosol formulation according to claim 1 further comprising about 0.3 percent by weight menthol.

11. An aerosol formulation according to claim 1 comprising from about 0.2 percent to about 0.5 by weight flunisolide, from about 10 to about 20 percent by weight ethanol, and 1,1,1,2,3,3,3-heptafluoropropane.

12. An aerosol formulation according to claim 11 comprising from about 0.2 percent to about 0.5 percent by weight flunisolide, from about 10 to about 20 percent by weight ethanol and from about 0.001 percent to about 0.005 percent by weight sorbitan trioleate.

13. An aerosol formulation according to claim 1 comprising from about 0.2 percent to about 0.5 by weight flunisolide, from about 10 to about 20 percent by weight ethanol, and 1,1,1,2-tetrafluoroethane.

14. An aerosol formulation according to claim 13 comprising from about 0.2 percent to about 0.5 percent by weight flunisolide, from about 10 to about 20 percent by weight ethanol and from about 0.001 percent to about 0.005 percent by weight sorbitan trioleate.

15. A method of treating bronchial asthma comprising administering via inhalation an amount of a formulation according to claim 1 sufficient to treat bronchial asthma.

16. A metered dose inhaler comprising: (i) an aerosol canister defining a formulation chamber; and (ii) a formulation according to claim 1, wherein said formulation is contained within said formulation chamber.

17. An inhaler according to claim 16, wherein the formulation chamber is coated with a resin that is inert to flunisolide.

18. An inhaler according to claim 17, wherein the resin is an epoxy resin.

19. An inhaler according to claim 16, wherein the aerosol canister is glass.

* * * * *